United States Patent [19]

Pitkin

[11] Patent Number: 5,405,408
[45] Date of Patent: Apr. 11, 1995

[54] ARTIFICIAL KNEE HAVING DUAL FLEXION ACTION DURING LOCOMOTION

[76] Inventor: Mark R. Pitkin, 32-3 Bayberry Dr., Sharon, Mass. 02067

[21] Appl. No.: 62,242

[22] Filed: May 14, 1993

[51] Int. Cl.⁶ .......................... A61F 2/64; A61F 2/38
[52] U.S. Cl. ...................................... 623/44; 623/46; 623/39; 623/20; 403/121; 403/145
[58] Field of Search .............. 623/44, 46, 20, 39; 403/121, 111, 145, DIG. 8

[56] References Cited

U.S. PATENT DOCUMENTS

| | | | |
|---|---|---|---|
| 3,453,663 | 7/1969 | Minor . | |
| 3,533,651 | 10/1970 | Prahl . | |
| 3,945,053 | 3/1976 | Hilberry et al. | 403/121 X |
| 4,065,815 | 1/1978 | Sen-Jung . | |
| 4,152,787 | 5/1979 | Meggyesy . | |
| 4,267,608 | 5/1981 | Bora | 623/21 |
| 4,428,369 | 1/1984 | Peckham et al. | 602/16 |
| 4,658,927 | 8/1987 | Haupt | 623/44 |
| 4,685,926 | 8/1987 | Haupt | 623/43 |
| 4,756,712 | 7/1988 | Clover, Jr. | 623/39 |
| 4,756,713 | 7/1988 | Cooper | 623/44 |
| 4,815,911 | 3/1989 | Bengstsson et al. | 414/7 |
| 4,846,841 | 7/1989 | Oh | 623/23 |
| 4,846,842 | 7/1989 | Connolly et al. | 623/43 |
| 4,888,021 | 12/1989 | Forte et al. | 623/20 |
| 4,911,709 | 3/1990 | Marlow et al. | 623/39 |
| 5,037,444 | 8/1991 | Phillips | 623/55 |
| 5,062,856 | 11/1991 | Sawamura et al. | 623/24 |
| 5,062,857 | 11/1991 | Berringer et al. | 623/25 |
| 5,062,858 | 11/1991 | Broeck et al. | 623/43 |
| 5,086,541 | 2/1992 | Auternaud et al. | 16/227 |

OTHER PUBLICATIONS

M. R. Pitkin, "Rolling Joint Prosthetic Foot and Ankle With Self Controlled Rigidity Of Elastic Ties", AAOP Symposium, Mar. 30–Apr. 3, 1993.

USSR Inventor's Certificate No. 820822, Apr. 15, 1981.

P. G. van de Veen, "A Polycentric Stance Phase Flexion Prosthetic Knee Mechanism", ISPO Proceedings, Jun. 28–Jul. 3, 1992, p. 175.

M. R. Pitkin, et al. "A Prototype Of The Rolling Joints Prosthetic Foot", ISPO Proceedings, Jun. 28–Jul. 3, 1992, p. 134.

Protex brochure, "A single-axis knee unit of dual action, normalizing the walk on an above-knee prosthesis (MN 4.13M)".

"A Single Axis Knee Unit of Dual Action Normalizing the Walk on an Above-Knee Prosthesis", (Protex Company Ltd. brochure).

*Primary Examiner*—David H. Willse
*Attorney, Agent, or Firm*—Weingarten, Schurgin, Gagnebin & Hayes

[57] ABSTRACT

An artificial knee having a dual flexion action during locomotion is disclosed. The knee comprises a femur part and a tibia part capable of rolling over each other in two different ways depending on whether or not the artificial leg is loaded. Pressure exerted on a cam surface of the femur part flattens the curvature of the cam surface, limiting the angle of rotation of the artificial knee when the knee is loaded. The parts are connected by elastic ties which are fixedly connected to the femur part and movably connected to the tibia part. When the knee is loaded, depending arms from the femur part contact the movable tibia connection and increase the elongation of the elastic ties, thereby additionally resisting rotation.

5 Claims, 4 Drawing Sheets

ARTIFICIAL KNEE HAVING DUAL FLEXION ACTION DURING LOCOMOTION

FIELD OF THE INVENTION

The present invention relates to the field of prosthetics, and, in particular, to a biomechanical prosthetic knee to assist an amputee in walking, running, and other types of locomotion.

BACKGROUND OF THE INVENTION

A real knee exhibits two types of flexing actions during locomotion, depending on whether it is unloaded or loaded. Locomotion comprises a swing phase, when the leg is lifted off the ground, and a stance phase, when the foot contacts the ground. In the swing phase, the knee is unloaded and is capable of almost free flexion, being able to swing as much as 60° to 70°. In the stance phase, the knee is loaded, and the knee's flexion ability is limited to no more than about 10° to 20°.

A graph of the vertical component of the ground reaction force, $F_y$, on a person's leg during the stance phase of locomotion is illustrated in FIG. 6a, and the approximate orientation of the leg during the stance phase is illustrated in FIG. 6b. As the leg initially contacts the ground, $F_y$ increases from 0 to a first peak. The knee is only slightly flexed, the angle of flexion being braked or limited during the stance phase of a real knee. The magnitude of $F_y$ at the first peak is slightly greater than the patient's weight, W, during walking, as seen in FIG. 6a. $F_y$ can be approximately three times the patient's weight during running. $F_y$ decreases slightly during the middle of the stance phase $F_y$ then increases to a second peak, approximately of the same magnitude as the first peak, and the knee is flexed slightly in preparation for the greater flexion during the swing phase, which occurs when $F_y$ decreases to 0 and the foot lifts off the ground.

It has been a challenge to create a prosthetic knee unit capable of this dual action: almost free flexion within 60°–70° during swing phase and flexion within 10°–20° during stance phase. Preliminary feasibility studies, by L. D. Fisher and G. W. Judge, indicate that prosthetic knee stance phase flexion results in shock absorption and reduces the vertical motion of the center of mass of the body. A knee design based on this work has a monocentric, load-activated brake joint with a torsional elastic coupling between the main axis and the brake drum. This knee provides a stance phase flexion similar to that of a sound gait, but a resistive element demonstrates dissipative behavior, which does not fully resemble the elastic behavior of the human knee. Another disadvantage is that the stability of the knee is reduced, while the flexion angle during the stance phase increases.

A dual-action artificial knee achieved with a single-axis design is disclosed by A. P. Kuzekin et al. However, this knee may be unstable and potentially dangerous in actual use, because triggering of the action is controlled by the prosthesis's foot position.

Increased stability has been achieved in polycentric knee mechanisms using four-bar and five-bar-linkages, disclosed in Van de Veen, P. G., Wagner, H., Krieger, W., "A Polycentric Stance Phase Flexion Prosthetic Knee Mechanism," *Proc. of the Seventh World Congress of ISPO*, Chicago, Ill., Jun. 28–Jul. 3, 1992, p. 175. But these as well as all other multi-axis knees comprise redundant links, which are difficult to manufacture and maintain.

A prosthetic foot has been designed using non-congruent rolling joint surfaces combined with and held together by linear elastic springs which more closely mimic actual joint motion, as disclosed in U.S.S.R. Inventor's Certificate No. 820,822, of M. R. Pitkin and I. A. Mendelevich, entitled "Artificial Foot." A "rolling joint" approach has also been used in U.S. patent application Ser. No. 07/947,919, of the present inventor entitled "Artificial Foot and Ankle," the disclosure of which is incorporated herein by reference. The basic mechanical principles used in the artificial foot and ankle are discussed with reference to FIGS. 1 and 2.

A rolling joint of an ankle or toe between an upper bone 2, e.g., a tibia, and a lower bone 4, e.g., a talus, is shown in FIG. 1. The joint is joined by an elastic tie or spring 6, illustrated in the initial, unloaded or neutral, position, by the line segment $OM_0$ having a length $l_0$.

In the initial state, shown by a solid line, the upper bone's articular surface contacts the lower bones's articular surface at point $K_0$. Due to a clockwise rotation of the upper bone, an arc with a center $C_0$ and radius $r=C_0K_0$ rolls along the surface of the bottom bone's articular surface. Contact between the bones occurs at point $K_1$.

The rotation causes the elastic tie at position $M_0$ to shift to position $M_1$ along a cycloidal path, which causes a tension force $T=\mu\Delta l$ in the spring, now at $OM_1$, where $\Delta l = l_1 - l_0$ and $l_1 = OM_1$. The instantaneous arm $L(\alpha) = K_1N$ of the force T increases as the angle $\alpha$ of rotation of the upper bone increases; $L(\alpha)$ does not remain equal to $K_0O$ as it would in a simple hinge rotatable about a fixed point.

Since the moment M of the force T is determined as $M = TL(\alpha)$, we obtain after calculation of $L(\alpha)$:

$$M = \mu \frac{(\sqrt{r^2(\alpha - \sin\alpha)^2 + (l_0 + r(1 - \cos\alpha))^2} - l_0)(l_0 + r\alpha)(l_0 + r(1 - \cos\alpha))}{\sqrt{r(\alpha - \sin\alpha)^2 + (l_0 - r(1 - \cos\alpha))^2}} \quad \text{if } |\alpha| > \alpha_0$$

$$M = 0 \quad \text{otherwise}$$

where the value of $\alpha_0$ corresponds to the initial position of the joint before the deflection affecting the tie 6, at $OM_0$.

As analysis shows, the diagram of M will always be convex downward, as seen in FIG. 2a. FIG. 2b provides a graphical illustration for $l_0 = 0.01$ m, $\mu = 3 \times 10^4$ N/m. Three curves are shown, for $r = 0.05$ m, $r = 0.10$ m and $r = 0.20$ m.

As seen in FIG. 2, when the angular deflection $\alpha$ of a joint approaches the natural limit of its range of motion (B+,B−), as motion continues and $|\alpha| \geq \alpha_0$, the moment M of ligament resistance increases rapidly and nonlinearly. This saturation, or increase in resistance, of the cam structure occurs because the point of contact of the elements during flexing has a horizontal component of the relative rolling motion between the contacting surfaces. The rolling joint may also be considered to be a succession of hinged two-element systems, the arm of each of which is greater than the arm of the previous system.

Even though the zones or areas at which the elastic ties are attached in this foot and ankle unit are movable with respect to each other for better control over the tension in the ties, this design cannot be directly applied to an artificial knee, because of the dual character of knee flexion: relatively small amortization flexion during stance phase and relatively large flexion during swing phase. Thus, a need still exists for a knee design which provides the dual action observed in a normal gait.

SUMMARY OF THE INVENTION

In view of the foregoing, the present invention applies a biomechanical emulation of the two different types of knee joint flexion during swing and stance phases to mimic real knee joint movement in the artificial knee, resulting in a more normal gait and a more natural sequence of joint mobility in both the swing and the stance phases.

The artificial knee of the present invention comprises an upper, femur, part and a lower, tibia, part capable of rolling in two different ways on each other depending on whether or not the artificial leg is loaded. The femur part includes a lower convexly curved cam surface and the tibia part an upper convexly curved cam surface. The cam surfaces of the respective parts contact each other at a point. The parts roll over one another without slipping, and the point of contact between the cam surfaces moves accordingly.

The femur and tibia parts are also connected by extensible elastic ties which are attached to the femur and tibia parts at zones or areas which are movable relative to each other in part due to the rolling motion over the cam surfaces. Also, the tibial attachment is provided by a "floating" or movable tibial hook which provides an additional component of motion between the attachment zones. As the rolling motion occurs, the femur attachment zone traces a curve, which can be derived from the following equations of general cycloidal motion:

$$x = a\Theta - h \sin \Theta,$$

$$y = a - h \cos \Theta,$$

where "a" is the radius of curvature of a circle rolling over a flat surface, "h" is the distance between the center of curvature and the femur attachment zone, and "$\Theta$" is the angle of rotation. The curve traced by the femur attachment zone is epicycloidal, because both the femur and tibia surfaces are convexly curved. Also, since the tibial attachment zone is additionally movable, the constant "a" in the above equations varies according to the position of the tibial attachment zone.

The femur part also includes a pivoting lever having depending arms which contact and move the floating tibial hook, thereby transferring a portion of patient's body weight to the tibial hook during the stance phase. The femur lever also presses on the femur cam surface, thereby changing the curvature of the femur cam surface. The lever makes the femur cam surface more or less flat according to the magnitude of the load P applied by the patient's body on the lever during the stance phase. However, the lever does not affect the tibial hook or change the femur cam curvature during the swing phase. During the swing phase, the femur cam curvature remains maximal, i.e., it has a minimal radius of curvature, and the elongation of the elastic ties due to the rolling is minimal. This provides a larger range of mobility (ROM) and a less resistive torque in the swing phase, in comparison with a smaller ROM and a more resistive torque in the stance phase.

In the stance phase, the first peak of the vertical component, $F_y$, of the ground reaction force causes the attachment zones of the elastic ties between the femur and the tibia to move apart due to contact between the depending arms of the femur part with the floating tibial hook, thereby elongating the ties. Elongation of the ties increases the resistive torque, which brakes or limits the stance phase flexion. The divergence of the elastic tie attachment zones also provides additional shock absorption (amortization) when the foot stands on the walking surface. Flattening of the femur cam and concomitant increasing of the radius of curvature of the femur cam during the stance phase additionally increases the torque of resistance to the mobility (flexion) in the knee joint, which helps to increase the stability of the joint up to complete immobilization at a knee angle of 15° to 20°. The elasticity of the cam is typically chosen so that the cam becomes substantially flat under the maximum anticipated loading.

When the vertical component of the ground reaction force decreases, the elastic tie attachment zones between the femur and the tibia parts move closer, increasing the curvature of the femur cam. This increases the mobility in the knee, in order to start the stance phase knee extension. The second peak of the vertical component of the ground reaction force initiates the swing phase flexion. The amplitude of the swing phase flexion is self-controlled by the speed of the patient's gait and can be adjusted by choosing an appropriate elasticity of the ties in accordance with the patient's criteria.

In this manner, the present invention provides a prosthetic knee which has a more normal dynamic and kinematic pattern of human walking, running and other forms of locomotion.

BRIEF DESCRIPTION OF THE DRAWINGS

The invention will be more fully understood from the following detailed description taken in conjunction with the accompanying drawings in which.

DETAILED DESCRIPTION OF THE PREFERRED EMBODIMENTS

Figure 1:
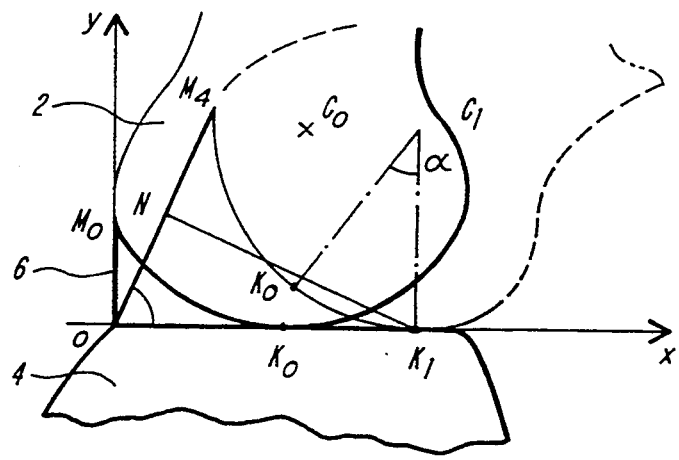
FIG. 1 is a schematic view of an analysis of a prior art rolling joint between a tibia and a talus.
Figure 2A:
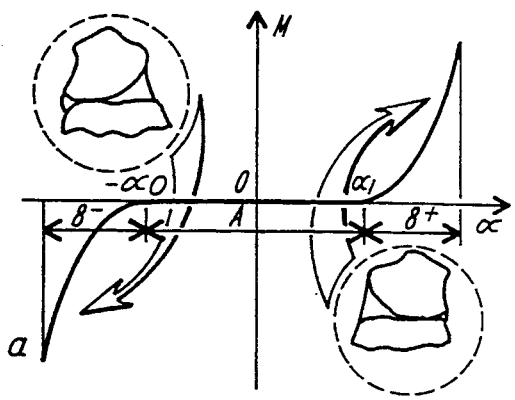
FIGS. 2a and 2b are graphs of the resistive moment versus angular deflection of the prior art rolling joint of FIG. 1.
Figure 2B:
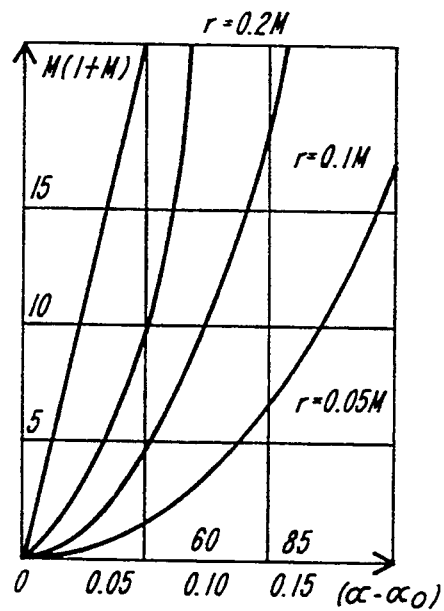
Figure 3:
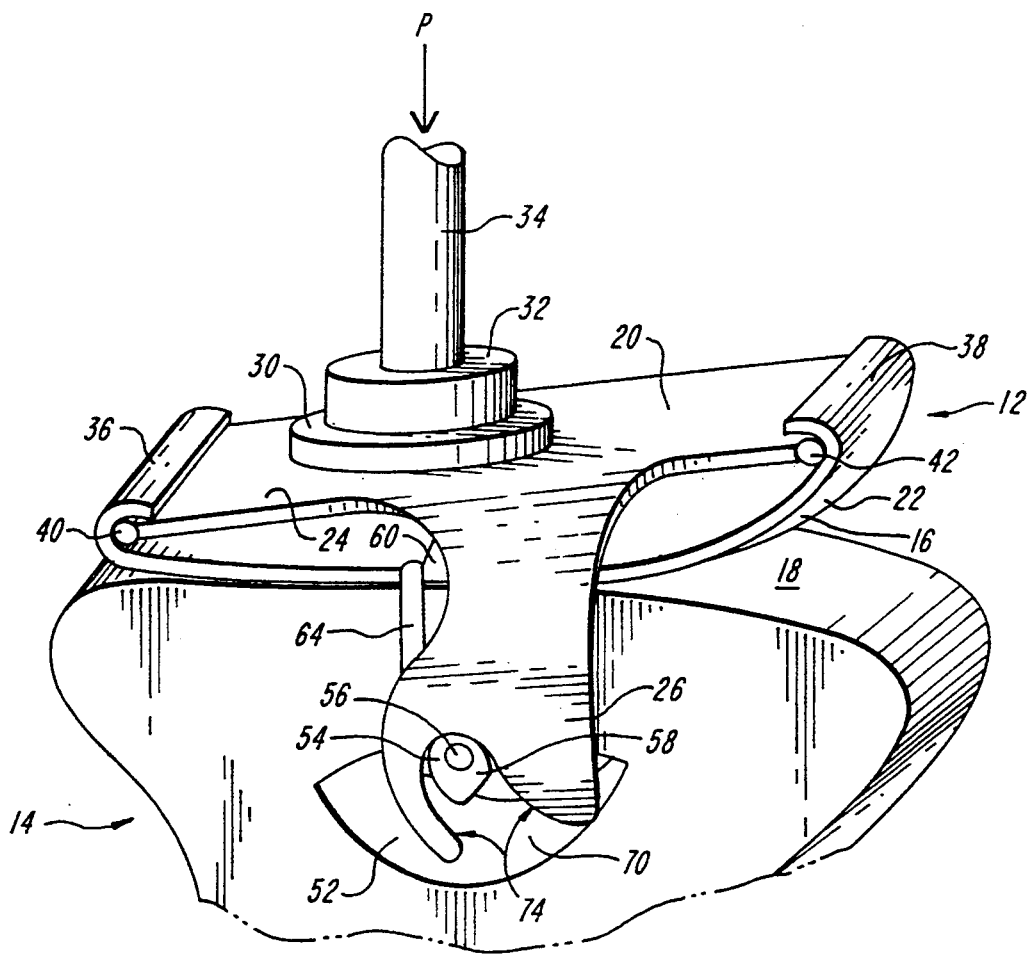
FIG. 3 is a perspective view of a prosthetic knee according to the present invention illustrating a neutral unloading.
Figure 4:
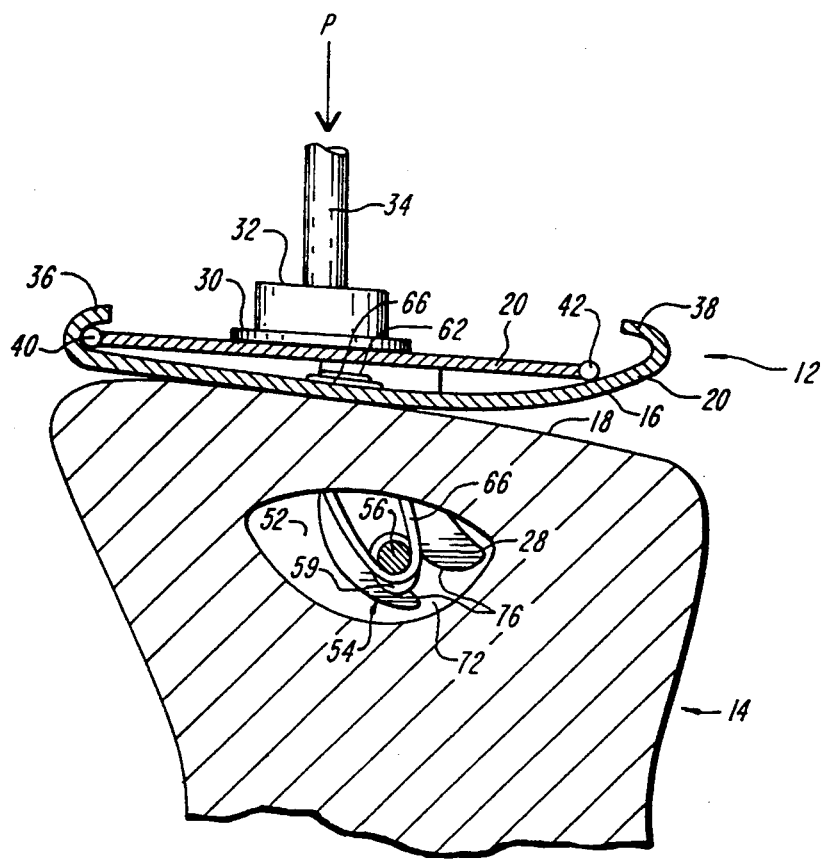
FIG. 4 is a cross-sectional side view of the invention of FIG. 3 illustrating a loaded condition.
Figure 5:
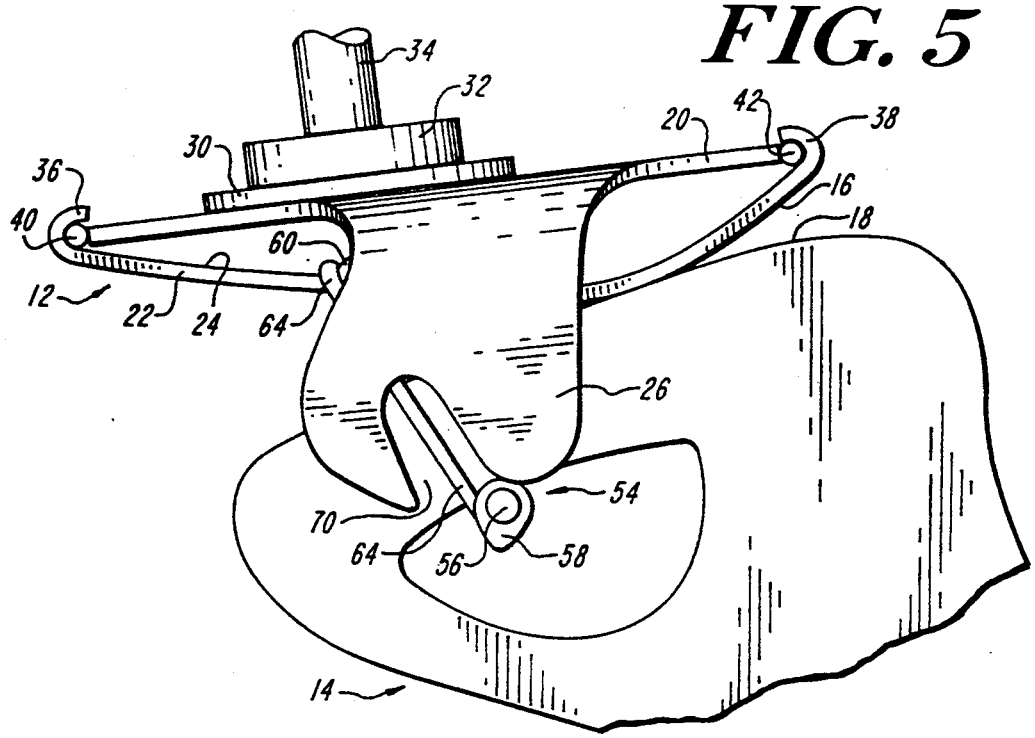
FIG. 5 is a side view of the invention of FIG. 3 illustrating an unloaded condition.
Figure 6A:
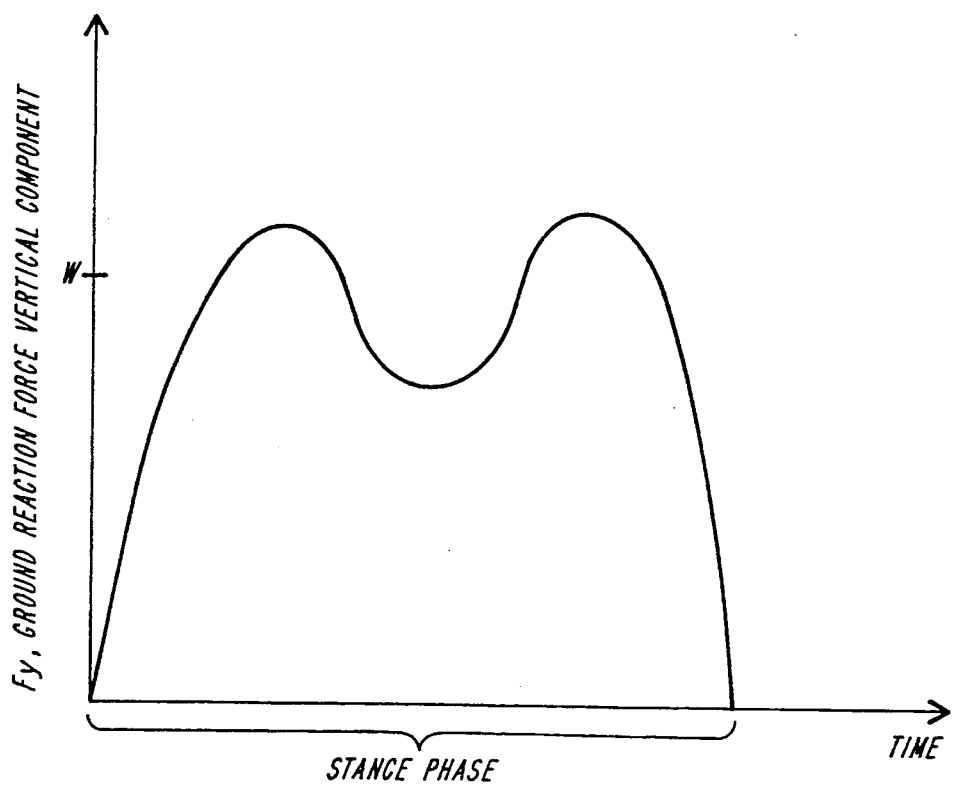
FIGS. 6a and 6b illustrate the vertical component of the ground reaction force on a patient's leg during locomotion.
Figure 6B:
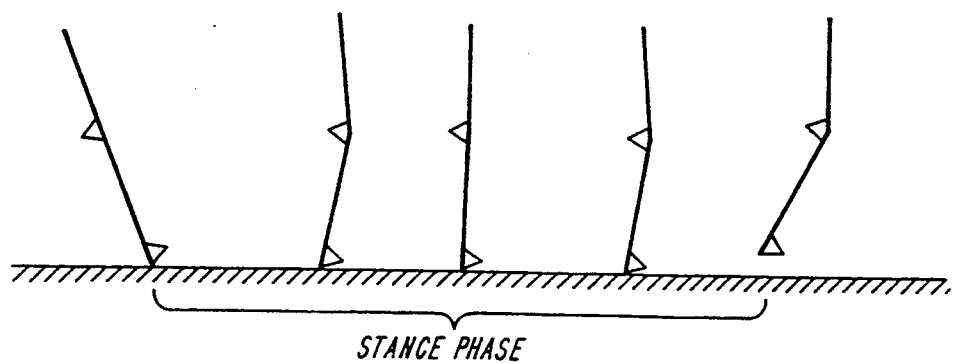

An artificial knee according to the present invention is shown in FIGS. 3 through 5, in which the front or anterior of the knee is toward the left. The knee comprises a femur part 12 and a tibia part 14 which are in rolling contact along articular surfaces 16, 18. The femur part comprises a relatively rigid lever member 20, formed for example of a metal or a composite material, and a relatively elastic cam member 22, formed for example of a carbon fiber composite material. The lever member comprises a flat plate 24 and depending medial and lateral arms 26, 28. A socket 30 on the upper surface of the flat plate receives a femur connector 32, whereby the artificial knee may be attached to a patient's femur 34. The knee may be attached to the femur in any other suitable manner known in the art.

The surface 16 on the cam member 22 of the artificial knee comprises a cam surface which extends lengthwise from front to back. At each end of the cam surface 16, the cam member 22 is sharply curved inwardly to form an anterior fixator 36 and posterior fixator 38. The lever member 20 is fixedly retained on the cam member 22 by an anterior hinged joint 40 sized to be fixedly received within the concave surface of the anterior fixator 36. A posterior roller 42 is formed on the opposite end of the lever member. The posterior roller is prevented from traveling beyond the posterior edge of the cam member by the posterior fixator 38. The anterior and posterior fixators 36, 38 restrict the mobility during the swing phase of the knee, when the knee is unloaded and the leg is lifted off the ground. FIG. 3 illustrates a knee under a neutral unloading (P=O) when the leg is straight; FIG. 5 illustrates an unloaded leg when the knee is substantially fully bent. As is apparent from FIGS. 3 and 5, the point of contact between the cam member and the tibia part moves from the anterior to the posterior of the knee as the knee is bent.

The tibia part 14 has an opening 52 extending from the lateral to the medial side. A tibial hook 54 extends freely through the opening to define a tibial zone of attachment for elastic ties to be described more fully below. The tibial hook comprises a bar 56 which extends a short distance beyond the opening on the lateral and medial sides of the tibia part. A retaining plate 58, 59 is formed near each end of the bar 56.

Upstanding femoral hooks 60, 62 are formed on each edge of the cam member 22 to define a femoral zone of attachment. On each side of the knee, an elastic tie 64, 66 is hooked over the corresponding femoral hook 60, 62 of the femur part. The elastic ties are also hooked over the tibial hook 54 which extends through the tibia part. The elastic ties are retained on the tibial hook by the corresponding retaining plates 58, 59. The ties may be formed, for example, from latex surgical tubing, which is known in the art. Surgical tubing is available in a wide variety of diameters and is quiet and reliable.

The elastic ties 64, 66 retain the tibia part 14 in contact with the femur part 12, while allowing some rolling motion therebetween. In addition, as pressure is placed on the lever member 20 by the patient loading P on the femur connector 32, as in the stance phase, the cam member 22 extends and tends to flatten out, as shown in FIG. 4. The greater P is, the more the cam member tends to flatten. This flattening restricts the angular range of motion of the knee. The posterior roller 42 restricts mobility during the stance phase and facilitates mobility during the swing phase. Further, slots 70, 72 defining cam surfaces 74, 76 provided in the ends of the lateral and medial depending femoral arms 26, 28 engage the tibial hook 54 just exterior to the retaining plates 58, 59. Since the tibial hook 54 is freely floating within the opening 52, the cam surfaces 74, 76 of the depending arms engage the tibial hook 54 and move the bar 56 down within the opening 52 against a restoring force provided by the elastic ties 64, 66. The greater the load P, the lower within the opening 52 the tibial hook 54 is pressed and the tighter the elastic ties 64, 66 become. The lower surface of the opening 52 may be located so that it is does not interfere with the tibial hook at its lowest expected point of travel when engaged by the depending arms 26, 28.

The femur connector 32 is located on lever member 20 in such a way that its vertical projection is positioned slightly anterior to the initial zone of contact between the femur part 12 and tibia part 14, as best seen in FIG. 3. Additionally, the elasticity of the elastic cam member 22 is chosen to substantially flatten during the stance phase such that, in combination with the force due to the femur connector, the lever member 20 rotates about the anterior joint 40 rather than rolling over the surface 18 of the tibial part 14. Resistance to the rotation, to brake the stance phase knee flexion, is provided by deformation of the elastic cam member 22 due to pressure from the roller 42 of the lever member 20 and by the extension of the elastic ties 64, 66, due to the force on the floating tibial hook 54 from the posterior edges of the slots 70, 72 in medial and lateral arms 26, 28 (FIG. 4). Specifically, the elasticity of the cam member is chosen such that the cam is substantially flattened under the maximum loading, which is typically three times the patient's weight, P=3 W, as shown in FIG. 4, and is most curved under no loading, P=0, as shown in FIG. 5.

As long as the load on the knee is increasing, rolling of the femur part 12 over the tibia part 14 is prevented by the previous deformation of the elastic cam member 22 which flattens the cam surface 16. This flattening results in extra braking of the movement, until a balance between the load and the resistance is reached.

At the middle of the stance phase, the vertical component of the ground reaction force, and accordingly the load applied to the leg, reaches a maximum and begins to decrease. The femoral hooks 60, 62 and tibial hook 54 accordingly elastically move closer. This helps to start the stance phase knee extension. At the same time, decreasing pressure by the roller 42 on the cam surface 16 increases the curvature of the cam member 22, which prepares the knee unit for the following swing phase flexion. Elastic limitation in the stance phase knee extension initiates a swing phase knee flexion.

The second peak of the vertical component of the ground reaction force occurs when the leg is in the rear position. It provides a flexing torque against the zone of contact of the cam member 22 and upper surface 18 of the tibia part 14. The swing phase knee flexion has a larger amplitude than during the stance phase, since the curvature of the cam member 22 has been increased, and the distance between the femoral hooks 60, 62 and tibial hook 54 is minimal. Elastic limitation in the stance phase knee extension makes an additional contribution in the swing phase knee flexion. The amplitude of the swing phase flexion is controlled by the speed of the patient's gait and the elasticity of the ties. The elasticity of the ties can be appropriately chosen in accordance with the patient's criteria, such as weight, length of residual limb, and level of activity.

As the femur part and tibia roll over the cam surfaces with respect to each other, the femoral zone of attachment traces out an epicycloidal curve which can be derived from the following equations of general cycloidal motion:

$$x = a\Theta - h \sin \Theta,$$

$$y = a - h \cos \Theta,$$

where "a" is the radius of curvature of a circle rolling over a flat surface, "h" is the distance between the center curvature and the femoral zone of attachment, and "Θ" is the angle of rotation. The curve traced by the femoral attachment zone is epicycloidal, because both the femur and tibia surfaces 16, 18 are convexly curved. Also, since the tibial attachment zone at tibial hook 54 is additionally movable, the constant "a" in the above equations varies according to the position of the tibial attachment zone.

Protection from hyperextension under the load is provided by the anterior and posterior fixators 36, 38 and the almost flat shape of the cam member 22 between the joint 40 and the zone of initial contact of the femur and the tibia in the neutral (unloaded) position. During swing phase knee extension, an additional protection from hyperextension is provided by the possible elongation of the elastic ties 64, 66 due to the pressure applied from the anterior edges of the slots 74, 76 on the tibial hook 54 moving in the opening. Thus, the controlled elasticity in the ties 64, 66 and controlled curvature of the contacting surfaces 16, 18 provide an artificial knee capable of exhibiting a dual action.

The invention is not to be limited by what has been particularly shown and described, except as indicated by the appended claims.

I claim:

1. An artificial knee comprising:
    a femur part comprising a flexible cam member which flexes to become flatter upon application of a force on said femur part;
    a tibia part having a surface disposed for rolling contact with said flexible cam member; and
    an elastic interconnection between said femur part and said tibia part, said elastic interconnection being movably connected to said tibia part at a movable tibia attachment and fixedly connected to said femur part at a fixed femur attachment;
    wherein said femur part further comprises a lever having an anterior end and a posterior end, said lever being fixedly mounted to said flexible cam member for rotation about said anterior end, said posterior end of said lever disposed to move over an upper surface of said flexible cam member;
    wherein said lever further comprises lateral and medial arms which depend from said lever to cooperatively engage said movable tibia attachment on said tibia part.

2. An artificial knee comprising:
    a tibia part having an upper curved surface;
    a femur part having a curved surface disposed to contact said upper curved surface of said tibia part along a contact area, said contact area being movable as said femur part rotates with respect to said tibia part, said curved surface further being flexible to become flatter upon application of a force on said femur part, whereby angle of rotation of said femur part with respect to said tibia part becomes limited;
    means for elastically interconnecting said femur part and said tibia part, said elastic interconnecting means being movably connected to said tibia part at a movable tibia attachment and fixedly connected to said femur part at a fixed femur attachment, whereby said interconnecting means provides relative movement between said tibia attachment and said femur attachment;
    wherein said femur part further comprises means for engaging said interconnecting means upon application of the force on said curved surface for separating said movable tibia attachment and said fixed femur attachment.

3. An artificial knee according to claim 2, wherein said means for elastically interconnecting said femur part and said tibia part comprises elastic members attached to said movable tibia attachment and said fixed femur attachment to provide a restoring force against the separation of said movable tibia attachment and said fixed femur attachment upon engagement by said engaging means.

4. An artificial knee according to claim 3, wherein said engaging means comprises lateral and medial arms depending from said femur part having camming surfaces for engaging said movable tibia attachment.

5. An artificial knee comprising:
    a femur part comprising a flexible cam member which flexes to become flatter upon application of a force on said femur part;
    a tibia part having a surface disposed for rolling contact with said flexible cam member; and
    an elastic interconnection between said femur part and said tibia part, said elastic interconnection being movably connected to said tibia part at a movable tibia attachment and fixedly connected to said femur part at a fixed femur attachment;
    wherein said femur part further comprises a lever having an anterior end and a posterior end, said lever being fixedly mounted to said flexible cam member for rotation about said anterior end, said posterior end of said lever disposed to move over an upper surface of said flexible cam member;
    wherein said tibia part has a laterally extending opening therethrough and said movable tibia attachment comprises an elongated member disposed through said opening and having a retaining element on each end thereof for cooperative engagement with said elastic interconnection, whereby said elastic interconnection is movably connected to said tibia part;
    wherein said lever further comprises lateral and medial arms which depend from said lever, said arms each having a slot formed therein to cooperatively engage said elongated member, whereby said elongated member is movable with respect to said tibia part.

* * * * *